ID Patent [19]

Olsen

[11] Patent Number: 4,567,141
[45] Date of Patent: Jan. 28, 1986

[54] PLASMID VECTORS INCLUDING TN904

[75] Inventor: Ronald H. Olsen, Ann Arbor, Mich.

[73] Assignee: Microlife Technics, Inc., Sarasota, Fla.

[21] Appl. No.: 488,036

[22] Filed: Apr. 25, 1983

[51] Int. Cl.[4] .................. C12P 19/34; C12N 15/00; C12N 1/00

[52] U.S. Cl. .................. 435/91; 435/172.3; 435/317; 935/29; 935/56; 935/72; 935/73; 935/23

[58] Field of Search .............. 435/91, 172.3, 253, 435/317, 875; 935/29, 24, 56, 23, 72

[56] References Cited

U.S. PATENT DOCUMENTS 4,374,200  2/1983  Olsen ........................... 435/172
4,376,164  3/1983  Olsen ........................... 435/253
4,418,194 11/1983  Olsen ........................... 435/253

OTHER PUBLICATIONS

McCombie, "Genetic and Physical Characterization of Tn904", Dissertation Abstracts International, 43(6) p. 1732-B (1982).
McCombie et al, "Pseudomonas Streptomycin–Resistance Transposon Associated with R Plasmid Mobilization", Journal of Bacteriology, 155(1), pp. 40–48 (1983), Chem. Abst. 99: 116916b.
Chou, J., et al, Nature, 282:801–806 (1979).
Heffron, F., et al, Proc. Nat. Acad. Sci. USA, 74:702–706 (1977).
Heffron, F., et al, Cell, 18:1153–1163 (1979).
Ohtsubo, H., et al., Cold Spring Harbor Symp. Quant. Biol., 43:1269–1277 (1979).
Jorgenson, R. A., et al, Mole, Gen. Genet., 177:65–72 (1979).
Rothstein, S. J., et al, Cell, 19:795–805 (1980).
Rothstein, S. J. et al, Cold Spring Harbor Symp. Quant. Biol., 45:99–105 (1980).
Auerswald, E., et al., Cold Spring Harbor Symp. Quant. Biol., 45:107–113 (1980).
Berg, D. E., et al, Cold Spring Harbor Symp. Quant. Biol., 45:115–123 (1980).
Olsen, R. H. et al, J. Bacteriol, 113:772–780 (1973).
Campbell, A. D., et al, pp. 15–22, In A. I. Bukhari et al, Cold Spring Harbor Laboratories Cold Spring Harbor, NY (1977).
Hansen, J. B. et al, Bacteriol, 135:227–238 (1978).
Royle, P., et al, H. Bacteriol, 145: 145–155 (1981).
Crisona et al, J. Bacteriol, 142:701–713 (1980).
VanGijisegem and Toussaint, Plasmid, 7: 30–44 (1982).
Olsen R. H., J. Bacteriol, 133: 210–216 (1978).
Olsen R. H. et al, J. Bacteriol, 125:837–844 (1976).
Jacoby, G. A. et al, J. Bacteriol, 127: 1278–1285 (1976).
Klapwijik, P. M. et al, J. Bacteriol, 141: 129–136 (1980).
Jacoby, G. A. et al, Antimicrob. Agents Chemother, 6: 239–252 (1974).
Olsen R. H. et al, J. Bacteriol, 150: 60–69 (1982).
Washington, J. A., II et al, Manual of Clinical Microbiology, 2nd Edition, American Society for Microbiology, Washington, D.C. (1974).
Guerry et al, J. Bacteriology, 116: 1064–1066 (1973).
Heffron, F. et al, Cold Spring Harbor Symp. Quant. Biol., 45: 259–268 (1980).
Sutcliffe, J. G., Cold Spring Harbor Symp. Biol., 43: 77–90 (1979).

(List continued on next page.)

Primary Examiner—Thomas G. Wiseman
Assistant Examiner—John E. Tarcza
Attorney, Agent, or Firm—Ian C. McLeod

[57] ABSTRACT

Cloning vectors are described which include the streptomycin resistance ($Sm^r$) determinant derived from Tn904. A single site for the restriction endonuclease, AvaI, is present within the Tn904 determinant for $Sm^r$. A method is described for preparing the Tn904 containing cloning vectors through transposition of Tn904 to a parent cloning vector and then cloning of the $Sm^r$ gene into another vector segment. The cloning vector is important for inserting deoxyribonucleic acid segments, which encode for various characteristics such as chemical production, antibiotic resistance or bacterial cell properties, in the $Sm^r$ gene AvaI cleaved site and which normally provides a marker for identification of transformed strains of bacteria.

25 Claims, 7 Drawing Figures

OTHER PUBLICATIONS

Shipley, P. L. et al, J. Bacteriol, 123: 20–27 (1975).
Benveniste, R., et al., Annu. Revs. Biochem., 42: 471–506 (1973).
Kopecko, D. J. et al, Proc. Nat. Acad. Sci. USA, 72: 1373–1377 (1977).
Bolivar, F., et al, Gene, 2: 95–113 (1977).
Jubanputra, R. S. et al, J. Med. Microbiol, 7: 169–177 (1974).
Olsen, R. H. et al, J. Bacteriol, 128: 228–234 (1976).
Holloway, B. W. et al, Bacteriol Rev., 33: 419–443 (1969).
Chandler, P. M. et al, Mutat. Res., 23: 15–23 (1974).
Ooms et al, J. Bacteriol, 144: 32–91 (1980).
Macrina, F. L. et al, Plasmid, 1: 417–420 (1978).
Kobayshi, F. et al, Japan, J. Microbiol, 16: 15–19 (1972).
Barth et al, J. Bacteriol, 125: 800–810 (1976).
Hedges et al, Gene, 1: 241–253 (1977).
Hedges, R. et al, J. Gen. Microbiol, 86: 88–92 (1975).
Rubens et al, J. Bacteriol, 139: 877–882 (1979).
Nordstrom, K. et al, J. Bacteriol, 110: 562–569 (1972).
Uhlin, D., et al, Plasmid, 1:1–7 (1977).
Heffron, F., et al, Proc. Nat. Acad. Sci. USA, 72: 3623–3627 (1975).

PLASMID VECTORS INCLUDING TN904

BACKGROUND OF THE INVENTION

1. Field of the Invention

The present invention relates to plasmid cloning vectors having a site, derived from transposon Tn904, which is cleaved by the restriction endonuclease AvaI and which encodes for streptomycin resistance and to a method for producing the cloning vectors. The present invention particularly relates to cloning vectors including the AvaI site from Tn904 in a parent vector derived from pRO1600 and pBR322.

2. Prior Art

Many transposons have been described for procaryote microorganisms. These transposons may be divided into two groups based on the composition of their distal regions. One such group, typified by Tn3, was obtained from the R-plasmid, R1. The distal regions of its DNA are sequences comprised of 38 base pairs which occur in reverse orientation (Ohtsubo, H., et al. Cold Spring Harbor Symp. Quant. Biol. 43:1269–1277 (1979)). These base pairs are absolutely required for transposition and mutations in these regions cannot be complemented in trans for transposition to occur (Gill, R. et al. Nature 282:801–806 1979; Heffron, F. et al. Proc. Nat. Acad. Sci. USA 74:702–706 (1977); Heffron, F., et al. Cell 18:1153–1163 (1979); Heffron, F., et al. Proc. Nat. Acad. (1979)). This organization is in marked contrast to Tn5, a transposon encoding Kanamycin resistance. The distal regions of Tn5 are characterized by DNA sequences in reverse orientation of 1.5 kilobase pairs each and the region which encodes Kanamycin resistance extends internally from one of the distal repeated sequences to the central, non-repeated regions of the transposon (Jorgenson R. A., et al. Mole, Gen. Genet. 177:65–72 (1979); Rothstein, S. J., et al. Cell 19:795–805 (1980); Rothstein, S. J. et al. Cold Spring Harbor Symp. Quant. Biol. 45:99–105 (1980)). The genes associated with transposition have been shown to be encoded by the other reverse repeat sequence (Auerswald, E. et al. Cold Spring Harbor Symp. Quant. Biol. 45:107–113 (1980); Rothstein, S. J., et al. Cell 19:795–805 (1980); Rothstein R. J., et al. Cold Spring Harbor Symp. Quant. Biol. 45:99–105 (1980)). In addition, it has been shown that either of the inverted repeats of Tn5 can transpose independently of the rest of the transposon (Berg, D. E., et al. Cold Spring Harbor Symp. Quant. Biol. 45:115–123 (1980)). Thus, two groups of transposons differing significantly in the size and function of their distal regions have been observed although there remains, also, significant diversity of structure and function within either of the two groups.

Many R-plasmids exist as a single replicon while other R-plasmids have been shown to exist as separate components, one bearing the R-determinants specifying resistance to antibiotics and the other encoding transfer functions. These multi-component R-plasmids are called aggregates and another example of an aggregate R-plasmid would be the combination of a transferable and a non-transferable plasmid aggregate wherein both plasmids would transfer together in bacterial matings selecting for the transfer of the transfer-defective plasmid, Ohtsubo, H., et al. Cold Spring Harbor Symp. Quant. Biol. 43:1269–1277 (1979).

The mobilization of pRO161, a non-transferable plasmid, when Tn1 transposed from pRO161 to a sex factor maintained by the same host bacterium has been described, Ohtsubo, H., et al. Cold Spring Harbor Symp. Quant. Biol. 43:1269–1277 (1979); Olsen, R. H., et al. J. Bacteriol. 113:772–780 (1973). This activity of Tn1 may have been associated with the formation of Tn1-mediated cointegrates during conjugation which resolved into separate plasmids in the newly-formed transconjugants, Campbell, A. D., et al. pp15–22. In: A. I. Bukhari et al. Cold Spring Harbor Laboratories, Cold Spring Harbor, New York (1977); Hansen, J. B., et al., J. Bacteriol. 135:227–238 (1978); Royle, P., et al., J. Bacteriol. 145:145–155 (1981). Transposition of Tn1 from pRO161 to either *Pseudomonas aeruginosa* sex factor, FP2, or the R-plasmid, R388, subsequently facilitated mobilization of pRO161 by FP2::Tn1 (e.g., pRO271) or R388::Tn1 (e.g., pRO231). Thus, plasmid mobilization ability (Pma) is presumably due to transdiploid homology between the transfer proficient and defective components of the plasmid aggregate that occurs when both plasmids have a copy of Tn1.

Transposon-mediated plasmid donor ability (Pma) of a nonconjugal plasmid, has been reported for pRO161, Ohtsubo, H., et al. Cold Spring Harbor Symp. Quant. Biol. 43:1269–1277 (1979). The association of Pma with the transposition of Tn1 from pRO161 to the *P. aeruginosa* sex factor, FP2; the resulting FP2::Tn1 mobilized pRO161 was shown. In these reports, transconjugants from matings were described whose phenotype resembles the result of analogous mobilizations using different plasmids as reported by Crisona et al., Cold Spring Harbor Symp. Quant. Biol. 45:115–123 (1980). These phenotypes included the occurrence of unstable cointegrate plasmids formed from the sex factor and the Tra⁻ plasmid of the aggregate donor as well as the dissociation products of the cointegrate, i.e., sex factor and the Tra⁻ plasmids. Our previous results, then, with Tn1-mediated Pma, resembled those of Crisona et al. with Tn3, J. Bacteriol. 142:701–713 (1980).

A recent report of Van Gijsegem and Toussaint described the formation of R-prime plasmids in Enterobacteriaciae which is facilitated by the transposable element, mini-Mu, Plasmid 7:30–44 (1982). These authors showed the formation of RP4-primes which include hetero-DNA (derived in this case from the chromosome) whose termini are defined by mini-Mu in direct repeat orientation. This structure may be analagous to the cointegrate intermediate proposed by the prior art for transposon-mediated Pma. (Olsen, R. H. J. Bacteriol. 133:210–216 (1978); Olsen, R. H., et al. J. Bacteriol. 125:837–844 (1976); Crisona, N. J., et al. J. Bacteriol. 142:701–713 (1980)). It has been observed that plasmids of the IncP-1 and IncP-2 groups formed recombinants in a recombination deficient (recA) host (Jacoby, G. A., et al. J. Bacteriol. 127:1278–1285 (1976)). One of the examples they cited was a recombination between plasmids RP1 and pMG1 resulting in the acquisition of $Sm^r$ by RP1. They suggested that recombination occurred reflecting homologous insertion sequences on IncP-1. Tn904, the $Sm^r$-transposon described in this application has been useful for labeling the octopine-Ti plasmid of *Agrobacterium tumefacinens* (Klapwijk, P. M. et al. J. Bacteriol. 141:129–136 (1980)). However, Ooms et al. Cold Spring Harbor Symp. Quant. Biol. 45:99–105 (1980) found that the acquisition of Tn904 resulted in variable increases in the size of the target Ti plasmid. These authors suggested that the variable increase in size of the Ti plasmid subsequent to the addition of Tn904 might reflect amplification of the DNA sequence encoding Sm$^r$ during selection for high levels of streptomycin resistance (2 mg/ml).

The prior art has not constructed plasmid cloning vectors using Tn904. Such vectors would be very useful for allowing DNA to be inserted in the AvaI site with certainty that it was located in the site.

OBJECTS

It is therefore an object of the present invention to provide cloning vectors including an AvaI site encoding for streptomycin resistance which is derived from Tn904. It is further an object of the present invention to provide cloning vectors which are highly transposable, and which can include DNA in the AvaI site which encodes for various properties such as chemical production or antibiotic resistance. These and other objects will become increasingly apparent from the following description and from the Figures.

GENERAL DESCRIPTION

The present invention relates to a method for transposing a transposon by mating bacterial cells wherein the first cell contains the transposon in a first plasmid and the second cell contains a second plasmid which is receptive to the transposon the improvement which comprises: transposing transposon Tn904 in a first plasmid PLASMID-1::Tn904 to a second vector plasmid receptive to the transposon to form a second transconjugant plasmid VECTOR PLASMID-2::Tn904, wherein Tn904 encodes for streptomycin resistance in a site cleaved by AvaI. The method also contemplates reducing the size of the Tn904 segment of the vector while retaining the AvaI site.

The present invention further relates to a cloning vector plasmid including deoxyribonucleic acid which encodes for streptomycin resistance in a site cleaved by AvaI and derived from Tn904. The vectors are preferably between about 5 and 10 kilobase pairs in length.

Bacterial strains were constructed which contained plasmids pRO161 and pMG1, which are respectively defective and proficient in self-transfer. It was expected that pMG1, an IncP-2 plasmid which transfers at a high frequency (Jacoby, G. A. Antimicrob. Agents Chemother. 6:239-252 (1974)), would acquire transposon Tn1, and thereby show Pma towards pRO161. However, contrary to expectations, a pMG1 R-determinant encoding streptomycin resistance (Sm$^r$) was in every instance added to pRO161 concurrent with its mobilization by pMG1. The Sm$^r$ was located on a transposon, which was designated Tn904. Cointegrate plasmids occurring as a consequence of Tn904-mediated Pma were not observed although, Tn904-facilitated cointegration of the plasmids may be so unstable as to preclude their detection.

Tn904, a transposon that encodes resistance to streptomycin was derived from the Pseudomonas plasmid, pMG1 (Jacoby, G. A. Antimicrob. Agents Chemother. 6:239-252 (1974)). It resembles Tn3 in its size and organization and in the present application we describe its distal regions and the location of the region which encodes streptomycin resistance (Sm$^r$).

The present invention provides the facilitation of Pma with Tn904 transposition and also the transposition of Tn904 to several disparate parent plasmid cloning vectors. When Tn904 transposes into plasmids pBR322 or pRO1600 (Olsen, R. H. et al. J. Bacterial. 150:60-69 (1982)) and as described in my U.S. Pat. No. 4,374,200 and pending application Ser. Nos. 312,409 filed Oct. 19, 1981 and 312,515 filed Oct. 19, 1981 both of which are cloning vectors, the size of these plasmids is increased by approximately 5.2 kilobases. The resulting cloning vectors or derivatives thereof have an AvaI cleaved site which encodes for the streptomycin resistance and are very useful, particularly in Pseudomonas which do not usually exhibit Sm$^r$.

SPECIFIC DESCRIPTION

Bacterial Strains and Plasmids. The relevant properties of the bacterial strains and the plasmids used in this study are listed in Table 1.

TABLE 1

| Bacteria and Plasmids | |
|---|---|
| Bacterial Strain | Relevant Characteristics |
| *P. aeruginosa* | |
| PAO1c | prototroph |
| PAO2 | ser-3 |
| PAO25 | argF, leu-18 |
| PAO38 | leu-38 |
| PAO2003 | argH, recA |
| *P. putida* | |
| AC541 | Met$^-$, contains K plasmid |
| *P. fluorescens* | |
| PF0141 | His$^-$ |
| *E. coli* | |
| ED8654 | Met$^-$, hsdR |
| ROE531 | Met$^-$ |
| J53 | Met$^-$, Pro$^-$ |

TABLE 1-continued

| | | |
|---|---|---|
| AE85 | aroA, His$^-$, Leu$^-$ Trp$^-$, recA | |
| V517 | Contains standard plasmids | |

| Strain (Plasmid) | Relevant Characteristics | NRRL Number |
|---|---|---|
| PA02 (RP1) | Cb$^r$, Tc$^r$, Km$^r$, Tra$^+$ | P.a. 15310 |
| PA02 (pR0161) | Cb$^r$, Tc$^r$, Tra$^-$ | P.a. 15312 |
| PA02 (pR0165) | Cb$^r$, Tc$^r$, Sm$^r$, Tra$^-$ pR0161::Tn904 | P.a. 15313 |
| PA02 (pR0169) | Cb$^r$, Tc$^r$, Km$^r$, Sm$^r$, Tra$^+$, RP1::Tn904 | P.a. 15319 |
| PA02 (pR01600) | cryptic | P.a. 15314 |
| PA02 (pR01614) | | P.a. 15315 |
| PA02 (pR01742) | Sm$^r$, pR01600::Tn904 | P.a. 15176 |
| PA02 (pR01743) | Sm$^r$, pR01600::Tn904 | P.a. 15317 |
| AE85 (pBR322) | Cb$^r$, Tc$^r$ | E.c. 15320 |
| AE85 (pR01744) | Cb$^r$, Tc$^s$, Sm$^r$, PBR322::Tn904 | E.c. 15321 |
| AE85 (pR01745) | Cb$^s$, Tc$^r$, Sm$^r$, pBR322::Tn904 | E.c. 15322 |
| FP2 | Hg$^r$, sex factor | not deposited |
| pR0272 | Hg$^r$, Sm$^r$, FP2::Tn904, sex factor | not deposited |
| R388 | Tp$^r$ | not deposited |
| pR0232 | Tp$^r$, Sm$^r$, R388::Tn904 | not deposited |
| K | Cryptic, sex factor | not deposited |
| pR0302 | Sm$^r$, K::Tn904, sex factor | not deposited |
| R751 | Tp$^4$ | not deposited |
| PA02 (pMG1) | Gm$^r$, Sm$^r$, Su$^r$, Hg$^r$ | P.a. 15311 |
| PA02 (pR01723) | deleted pR01614 Cb$^r$ | P.a. 15316 |
| AE85 (pR01746) | pBR322::Tn904 Cb$^r$, Tc$^r$, Sm$^r$ | E.c. 15323 |
| AE85 (pR01747) | deleted pR01744 Cb$^r$, Tc$^s$, Sm$^r$ | E.c. 15324 |
| pR01723:pR01747 (pR01748) recombinant PA02 | Cb$^r$, Sm$^r$ | P.a. 15318 |

P.a. is *Pseudomonas aeruginosa*
E.c. is *Escherichia coli*

Marker abbreviations. Bacterial strains: arg, arginine; aro, aromatic amino acid; His, histidine; HsdR, K-12 restriction; leu, leucine; Met, methionine; Pro, proline; rec, recombination deficient; ser, serine; Trp, tryptophan. Plasmids: Cb$^r$, carbenicillin resistance; Tc$^r$, tetracycline resistance; Km$^r$, kanamycin resistance; Sm$^r$, streptomycin resistance; Gm$^r$, gentamicin resistance; Tm$^r$, tobramycin resistance; Su$^r$, sulfonamide resistance; Tp$^r$, trimethoprim resistance; Hg$^r$, mercuric ion resistance; Tra, conjugal transfer. The NRRL Number is from the Northern Regional Research Laboratory in Peoria, Illinois and all of the strains set forth herein are freely available to the public by reference to the strain and the NRRL number.

Media. Minimal medium (VBG) and complex medium (TN) were prepared as described previously (Olsen, R. H., et al. J. Bacteriol. 113:772–780 (1976)). Minimal medium was supplemented with amino acids to a final concentration of 0.5 mM except isoleucine-valine (0.26 mM) and tyrosine (0.1 percent final concentration). Thymine was added to a final concentration of 5 µg/ml. Thiamine was added to a final concentration of 1 µg/ml.

When antibiotics were used for the selection or characterization of *Escherichia coli* transconjugants, media were supplemented as follows: carbenicillin (Cb), 500 g/ml; streptomycin (Sm), 25 µg/ml; Kanamycin sulfate (Km), 30 µg/ml; trimethoprim (Tp), 100 µg/ml; and tetracycline (Tc), 25 µg/ml. For the selection of *P. aeruginosa*, antibiotics were added to the following concentrations: Cb, 500 µg/ml; Tc, 50 µg/ml; Sm, 250 µg/ml; Tp, 500 µg/ml; tobramycin (Tm), 5 µg/ml; and gentamicin (Gm), 10 µg/ml.

MIC determinations. MIC determinations were done essentially as described in the Manual of clinical Microbiology (Washington, J. A., II et al. Manual of Clinical Microbiology. Second edition. American Society for Microbiology. Washington, D.C. (1974)). Streptomycin was diluted into TN broth from a stock solution of freshly rehydrated antibiotic. Cultures to be tested were freshly grown on TN agar medium, suspended in TN broth nd inoculated into TN broth with streptomycin to $5 \times 10^4$ cells per ml. After mixing, the tubes were incubated at 37° for approximately 17 hours. Visible turbidity in a tube was indicative of resistance to the concentration of antibiotic contained in the growth medium.

Preparation and Characterization of Plasmid DNA. Plasmid DNA was prepared using a modification of the method of Guerry et al. J. Bacteriology 116:1064–1066 (1973); (Hansen, J. B., et al. J. Bacteriol. 135:227–238 (1978)). For rapid screening of transconjugants or transformed plasmids the method of Hansen et al. J. Bacteriology 135:227–238 (1978) was used. For physical mapping of the plasmids, their DNA was cleaved with restriction endonucleases as recommended by the supplier. Cloning of plasmid DNA or Pseudomonas chromosomal fragments is described herein or as reported previously (Olsen, R. H., et al. J. Bacteriol. 150:60–69 (1982) and as set forth in U.S. application Ser. No. 328,957, Filed Dec. 9, 1981.

Enzymes. Conditions for restriction endonuclease digestion were those as suggested by the supplier (Bethesda Research Laboratories, Gaithersburg, MD.).

Agarose Gel Electrophoresis. Plasmid DNA which had been cleaved with restriction endonucleases was electrophoresed as described previously (Heffron, F. et al. Cold Spring Harbor Symp. Quant. Biol. 45:259–268 (1980).

Electron Microscopy. Heteroduplex analysis of plasmid DNA was done based on a procedure of Davis, et al. J. Bacteriol. 116:1064–1066 (1973)). Plasmid pBR322, converted to open circular form by repeated freezing and thawing, was added to hyperphase to serve as an internal size standard for the estimation of the size of the heteroduplex figures. Grids were viewed on a Zeiss EM10 electron microscope and representative molecules were photographed. All photographs to be used for quantitative purposes were taken at the same magnification. All pBR322 size standards analyzed were intact circles. After the negatives were developed, the molecules were measured using a Numonics Digitizer. Each molecule was measured three times and the average of these determinations used as the length value. Size was determined based on a size of 4362 bp for the pBR322 size standard (Sutcliffe, J. G. Cold Spring Harbor Symp. Quant. Biol. 43:77–90 (1979)).

Bacterial Matings. To facilitate selection of transconjugants from matings which occur at low frequency, donor and recipient bacteria were grown overnight on the surface of TN agar as mixed cultures. The cells were then harvested from the surface of the plates, suspended in buffer and plated onto selective medium. Other bacterial matings were as described previously (Shipley, P. L. et al. J. Bacteriol. 123:20–27 (1975)).

Confirmation of the recA phenotype. The recA phenotype of *E. coli* strain AE85, was used to test transposition between plasmids, was confirmed by determining its sensitivity to ultraviolet light (Benveniste, R., et al. 42:471–506 (1973)). A wild-type *E. coli* K-12 and a recA *E. coli*, strain HB101 were used as controls.

Plasmid DNA transformation. *P. aeruginosa* was transformed using a modification of the procedure of Mercer and Loutit (Kopecko, D. J., et al. 72:1373–1377 (1975). *E. coli* was transformed using a modification of the procedure of Davis et al. Gene 2:95–113 (177) as previously described (Olsen, R. H. et al. J. Bacteriol. 150:60–69 (1982)).

Characteristics of Tn904

Mobilization of pRO161. In previous reports (Olsen, R. H. et al. J. Bacteriol. 133:210–216 (1978); Olsen R. H. et al. J. Bacteriol. 125:837–844 (1976), changes in mating behavior were described for the FP2/pRO161 R-plasmid aggregate subsequent to its formation and serial transfer. In the present work, a similar strategy was initially followed, using the IncP-2 incompatibility group R-plasmid, pMG1 (Jacoby, G. A., et al. Antimicrob. Agents Chemother. 6:239–252 (1974)), as the transfer proficient (Tra+) component of the aggregate, pMG1/pRO161. R-plasmid pMG1 is a limited host-range Pseudomonas plasmid originally described by Jacoby. Antimicrob. Agents. Chemother. 6:239–252 (1974) which encodes resistance to gentamicin, streptomycin, sulfonamide and mercury salts. It has been shown to be a large R-plasmid of approximately 312 Mdaltons (Hansen, J. B. et al. J. Bacteriol. 135:227–238 (1978). R-plasmid pRO161 is a Tra− deletion mutant of RP1 produced by transductional shortening of RP1 with bacteriophage P22 (Shipley, P. L., et al. J. Bacteriol. 123:20–27 (1975)). Table 2 shows plasmid mobilization ability (Pma) of pMG1 towards pRO161. The first mating listed illustrates the behavior of a newly constructed aggregate: selection of transconjugants for their acquisition of $Tc^r$ indicates mobilization of pRO161. Selection for the acquisition of gentamicin resistance ($Gm^r$) in this and subsequent matings indicates independent transfer of pMG1. Furthermore, the transfer frequency of pMG1 was unaffected by the presence of pRO161 in the newly constructed aggregate or in subsequent retransfers from transconjugants which also contained mobilized pRO161. This result suggests that pMG1 is not changed by either the co-maintenance of pRO161 or its prior mobilization of pRO161. The second mating listed in Table 2 shows however that the Pma of pMG1 towards pRO161 significantly increased following an initial mobilization of the aggregate: a transconjugant from the first mating, designated PAO2(pMG1/pRO161)A1, when used as donor for retransfer, now showed higher Pma towards pRO161 than the first mating listed in Table 2.

TABLE 2

Transfer and retransfer of the plasmid aggregate pMG1/pRO161[a]

| Donor | Selection[b] | Transconjugants per donor |
|---|---|---|
| PAO38(pMG1/pRO161) | Gm | $8 \times 10^{-2}$ |
|  | Tc | $9 \times 10^{-5}$ |
| PAO2(pMG1/pRO161)A1 | Gm | $5 \times 10^{-2}$ |

TABLE 2-continued

Transfer and retransfer of the plasmid aggregate pMG1/pRO161[a]

| Donor | Selection[b] | Transconjugants per donor |
|---|---|---|
|  | Tc | $4 \times 10^{-3}$ |

[a]For the first mating listed, PAO2 was the recipient. For the second mating listed, PAO38 was the recipient.
[b]Selection was on minimal medium supplemented with antibiotic (see Materials and Methods). Based on previous work, it was thought that this enhancement of Pma after one mobilization reflected transposition of Tn1 from pRO161 to pMG1 to create trans-diploid homology between the two plasmids (pMG1::Tn1 and pRO161) and subsequent host recombination-independent mobilization similar to that reported previously for plasmids RP2 (Olsen R. H. J. Bact. 133:210–216 (1978) and R388 (Shipley, P.C. and Olsen R.H. J. Bact. 123:20–27 (1975)).

To determine the nature of a possible Pma-associated change in the aggregate, incompatibility tests were done: the results are shown in Table 3. Recipients of the IncP-1 plasmid R751 (Jubanputra, R. S., et al. J. Med. Microbiol. 7:169–177 (1974) used to displace pRO161, were tested for maintenance of antibiotic resistances. The IncP-2 plasmid, pMG5 (Jacoby, G. A. Antimicrob. Agents Chemother. 6:239–252 (1974) was similarly used to displace pMG1. When pRO161 was displaced by R751, carbenicillin resistance ($Cb^r$) was lost. Therefore, Tn1 had not transposed to pMG1 and thus was not responsible for the facilitated mobilization of pRO161, unlike our previous observations of pRO161 mobilization by RP2. However, when pMG1 was displaced by pMG5, streptomycin resistance ($Sm^r$) was retained: this indicated that pRO161 had acquired $Sm^r$ as a consequence of its mobilization by pMG1. To test whether the $Sm^r$ determinant was now part of pRO161, we did transduction tests as described previously (Shipley, P. L., et al. J. Bacteriol. 123:20–27 (1975)) *P. aeruginosa* bacteriophage F116 (Holloway, B. W. et al. Bacteriol. Rev. 33:419–443 (1969)) was grown on PAO38 (pMG1/pRO161)A1 and three other aggregates similarly used for the serial retransfer experiment described in Table 2. Regardless of whether F116 transductants were selected for $Cb^r$, $Tc^r$ or $Sm^r$, each of the other two independent r-determinant markers were found to be cotransduced. This result suggested that the pMG1-$Sm^r$ determinant had been added to pRO161 concurrent with its mobilization by pMG1.

TABLE 3

Incompatability of PAO38(pMG1/pRO161)A1 with plasmids R751 and pMG5.

| Donor | Selection[a] | Phenotype of transconjugants with the donor plasmid[b] |
|---|---|---|
| J53(R751) | $Tp^r$ | $Cb^s, Tc^s, Sm^r, Gm^r, Hg^r, Tp^r$ |
| PF0141(pMG5) | $Tm^r$ | $Cb^r, Tc^r, Sm^r, Gm^s, Hg^r, Tm^r$ |

[a]Selection was on minimal medium supplemented with antibiotic (see Materials and Methods).
[b]Transconjugants from these matings were picked onto minimal medium with antibiotic as described in Materials and Methods. For testing of $Hg^r$, transconjugant colonies were picked onto $HgCl_2$ supplemented Brain Heart Infusion medium(Difco, Detroit, Michigan) (60 g/ml).

Reconstruction experiments were conducted to more specifically indicate whether the enhancement of Pma following an initial transfer of the pMG1/pRO161 aggregate resulted from changes in pMG1, pRO161 (in addition to its apparent acquisition of $Sm^r$) or both. The results of these experiments are shown in Table 4. In the first mating listed, the aggregate, PAO38(pMG1A1/pRO161) was formed by retransfer with selection for $Gm^r$ of pMG1A1, a pMG1 that had previously mobilized pRO161 to an intermediate host. Plasmid pRO161 was then added to the pMG1A1-containing bacterial strain by transduction. In the first mating listed in Table 4, it can be seen that the frequency of Pma for pMG1A1 towards pRO161 is low and similar to that observed for a newly formed aggregate shown in the first mating in Table 2. This result suggests that the enhancement of Pma observed for serially retransferred aggregates probably does not reflect a change in pMG1. However, the second mating listed in Table 4 does show the enhanced Pma characteristic of serially retransferred aggregates. In this instance, pRO161A1 (later designated pRO165) had previously been mobilized by pMG1 and had acquired $Sm^r$. This result suggests that acquisition of $Sm^r$ and the resulting trans-diploid homology extent between the Tra+ and Tra− components of the aggregate results in enhancement of Pma.

TABLE 4

Mating of reconstructed R-plasmid aggregates.

| Mating | Selection[a] | Trans-conjugants per donor |
|---|---|---|
| PA038(pMG1A1/pRO161)[b] × PA02 | $Gm^r$ | $8 \times 10^{-2}$ |
| | $Tc^r$ | $4 \times 10^{-5}$ |
| PA02(pMG1/pRO161A1)[c] × PA038 | $Gm^r$ | $9 \times 10^{-2}$ |
| | $Tc^r$ | $4 \times 10^{-3}$ |

[a]Selection of transconjugants was as described in Materials and Methods.
[b]This strain was constructed by mating a pMG1A1, a pMG1 plasmid that had previously mobilized pRO161 into strain PA038(pRO161), that contained a pRO161 never previously mobilized.
[c]This strain was constructed by phage F116 transduction of a previously mobilized pRO161 (designated pRO161A1) into a bacterial strain which contained pMG1 that had not mobilized pRO161 previously.

A determination was made to see if recombination activity by the host bacterium was required for enhancement of Pma towards pRO161 by pMG1. For this, we used a recA mutant of *P. aeruginosa*, strain PAO2003, which resembles similar mutants described previously for *Escherichia coli* (Chandler, P. M., et al. Mutat. Res. 23:15–23 (1974)). The results of mating either a newly constructed or a serially retransferred aggregate from PAO2003 are shown in Table 5.

TABLE 5

Mobilization of pRo161 from a recA donor to PAO2.

| Donor | Selection[a] | Transconjugants per donor |
|---|---|---|
| PA02003(pMG1/pRo161)[b] | $Gm^r$ | $3 \times 10^{-2}$ |
| | $Tc^r$ | $3 \times 10^{-5}$ |
| PA02003(pMG1/pRO161)A1[c] | $Gm^r$ | $1 \times 10^{-2}$ |
| | $Tc^r$ | $1 \times 10^{-4}$ |

[a]See Materials and Methods.
[b]This strain was constructed by phage F116 transduction of pRO161 to PAO203(pMG1).
[c]This strain was constructed by conjugally transferring the R-plasmid aggregate from PA038(pMG1/pRO161)A1 (see Table 2) to PAO2003.

Both strains listed in Table 5 showed Pma towards pRO161, suggesting that the acquisition of $Sm^r$ by pRO161 and subsequent mobilization occurs in the recombination-deficient genetic background, even though enhanced Pma from a recA donor for a serially retransferred aggregate is less than that observed in Rec+ donors. The acquisition of $Sm^r$ by pRO161 in the aggregate plasmids maintained in a recA genetic background suggests the behavior of a transposon. These results also suggest that the recombination-independent mobilization occurs as a function of trans-diploid transposon homology as reported previously for Tn1 (Olson, R. H. J. Bacteriol. 133:210–216 (1978)).

Tn904 Transposition. In view of the foregoing results, the putative $Sm^r$-transposon was designated as Tn904. It was next determined whether Tn904 would transpose to plasmids other than pRO161. In particular, the occurrence of Tn904 transposition in the recA bacterial strain, PAO2003 was demonstrated, as shown in Table 6. The first mating in Table 6 shows the strategy used for selection of an RP1::Tn904 plasmid (later designated pRO169). Since plasmid RP1 freely transfers from pseudomonads to *E. coli* (Olsen, R. H., et al. J. Bacteriol. 113:772–780 (1973)) wherein pMG1 does not (Olsen, R. H., et al. J. Bacteriol. 238:228–234 (1976)), transfer of the $Sm^r$ determinant to an *E. coli* recipient reflects the transposition of Tn904 to RP1 in a recA background. In the next three matings, plasmid pRO161::Tn904 (pRO165, described earlier) was used as a transposon donor to the *P. aeruginosa* sex factor, FP2 (Holloway, B. W. Bacteriol. Rev. 33:419–443 (1969)), to a broad host range R-plasmid, R388 (Shipley, P. L., et al non-transmissible antibiotic resistance plasmid by transductional shortening of R factor RP1. J. Bacteriol. 123:20–27 (1975)), to a broad host range R-plasmid, R388 (30), and to the *P. putida* sex factor, K. (Holloway, B. W. Bacteriol. Rev. 33:419–443 (1969)), to a broad host range R-plasmid, R388 (Shipley, P. L., et al. J. Bacteriol. 123:20–27 (1975)). Since pRO165 is Tra−, mobilization of $Sm^r$ reflects either transposition of Tn904 into the Tra+ companion plasmid of the aggregate or the mobilization of pRO165 by the Tra+ plasmid. That the latter possibility did not occur was indicated by failure to cotransfer of all the pRO165 markers (e.g., $Cb^r$, $Tc^r$, $Sm^r$). In the four matings in Table 6, testing of the transconjugants showed only the acquisition of $Sm^r$ with selection for that resistance. Therefore, Tn904 transposes to plasmids unrelated to RP1. With transposition to FP2, the second mating in Table 6, selection for $Cb^r$ was done also as an internal control to compare the transposition frequency of Tn1, located in plasmid pRO165, with that of Tn904: they were equivalent. In the fourth mating listed in Table 6, it was necessary to do a triparental mating since the *P. putida* sex factor, K. encodes no selectable markers. Typical transconjugants were selected from the four matings in Table 6 and the transconjugant plasmids were designated pRO272 (FP2::Tn904), pRO232 (R388::Tn904) and pRO302 (K::Tn904). These plasmids freely retransferred in serial matings and in the case of pRO272 and pRO302, their chromosome mobilization ability (Cma) was unimpaired.

TABLE 6

Transposition of Tn904 to other plasmids

| Mating | Aggregate plasmid donor | Recipient | Section[a] | Transfer frequency per donor[b] |
|---|---|---|---|---|
| 1 | PA02003(RP1/pMG1) | J53 | $Sm^r$(Tn904) | $1 \times 10^{-7}$ |
| 2 | PA02003(FP2/pRO165) | PA02 | $Cb^r$(Tn1) | $1 \times 10^{-7}$ |
| | | | $Sm^r$(Tn904) | $1 \times 10^{-7}$ |
| 3 | ED8654(R388/pRO165)[c] | ROE531 | $Sm^r$(Tn904) | $1 \times 10^{-7}$ |
| 4 | Triparental mating: AC541 × PA02003 (pRO165) × PA02 | PA02 | $Sm^r$(Tn904) | Unknown |

[a]See Materials and Methods
[b]This transfer frequency reflects the product of the transposition frequency and the transfer frequency of the target, transfer-proficient plasmids.
[c]This strain was constructed by transforming pRO165 into ED8654 (4) and subsequently adding plasmid R388 by conjugal mating.

Cloning Vectors From Tn904

EXAMPLE 1

The transposon Tn904 was transposed to pRO1600, a small multicopy crytpic plasmid described in U.S. patent application Ser. No. 147,563, Filed May 8, 1980, now U.S. Pat. No. 4,374,200. For this, pRO169 (RP1::Tn904) was mated into a *P. aeruginosa* strain containing pRO1600. DNA was then prepared from the aggregate plasmid-containing strain and used to transform strain PAO2 with selection for the acquisition of $Sm^r$. Most of the transformants obtained were only $Sm^4$ and thus putatively contained pRO1600::Tn904. Two pRO1600::Tn904 transformants, designated pRO1742 and pRO1743, were saved for physical mapping of the transposon.

EXAMPLE 2

Figure 1:
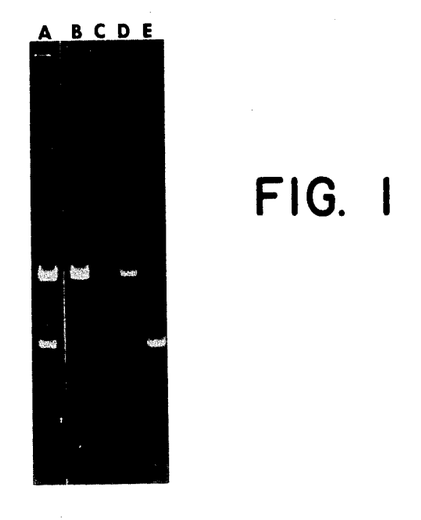
FIG. 1 shows agarose gel electrophoresis of Tn904 cloning vectors. DNA was prepared and electrophoresed as described hereinafter. Lane A, the plasmid aggregate pRO169/pBR322; Lane B, pRO1744; Lane C, multiple size standard plasmids of E. coli strain V5171; Lane D, pRO1745; Lane E, pBR322.

Experiments analagous to Example 1 were done with *E. coli* strain AE85, a recA mutant. Plasmid pRO169 was mated into AE85 which contained plasmid cloning vector pBR322 to form an aggregate: DNA was then prepared for transformation and selection of pBR322::Tn904. Selection was done for the acquisition of $Sm^r$ and the transformants were $Sm^r$ and either $Cb^r$ or $Tc^r$ or both. Thus, for some transformants, Tn904 had inserted into regions of pBR322 encoding either $Cb^r$ or $Tc^r$. Two of these transformants were selected for further study and designated AE85(pRO1744) and AE85(pRO1745). Strain AE85(pRO1744) had the phenotype $Sm^r$, $Tc^s$, $Cb^r$ and strain AE85 (pRO1745) was $Sm^r$, $Tc^r$, $Cb^s$. Another transformant designated AE85(pRO1746), was $Cb^r$, $Tc^r$ and $Sm^r$ was recovered. Therefore, the transposition of Tn904 was recA-independent in *E. coli* as well as in *P. aeruginosa*. Plasmid DNA of pBR322:Tn904 derivatives is shown in FIG. 1. Lane A shows DNA prepared from the plasmid aggregate, pRO169/pBR322, used later to select pRO1744 and pRO1745 transformants. The plasmid profile shown here was anomalous and unexpected. At the bottom of the lane is plasmid pBR322 and at the top plasmid pRO169. However, a band intermediate to the transposon-donor, pRO169, and the target plasmid, pBR322, is displayed whose size corresponds to that shown in lanes B and D for pRO1744 and pRO1745 respectively. It was surmised at this point that the donor-aggregate DNA used to transform and select the transposed-derivative plasmids probably contained a significant population of pBR322::Tn904 plasmids. This result did not obtain for donor-aggregate DNA extracted from Pseudomonas bacteria which contained the aggregate pRO169/pRO1600. In retrospect it is believed the result in FIG. 1 from the *E. coli* experiments is associated with the maintenance of the bacteria on medium which contained streptomycin (25 mg/ml), as discussed hereinafter.

Figure 2:
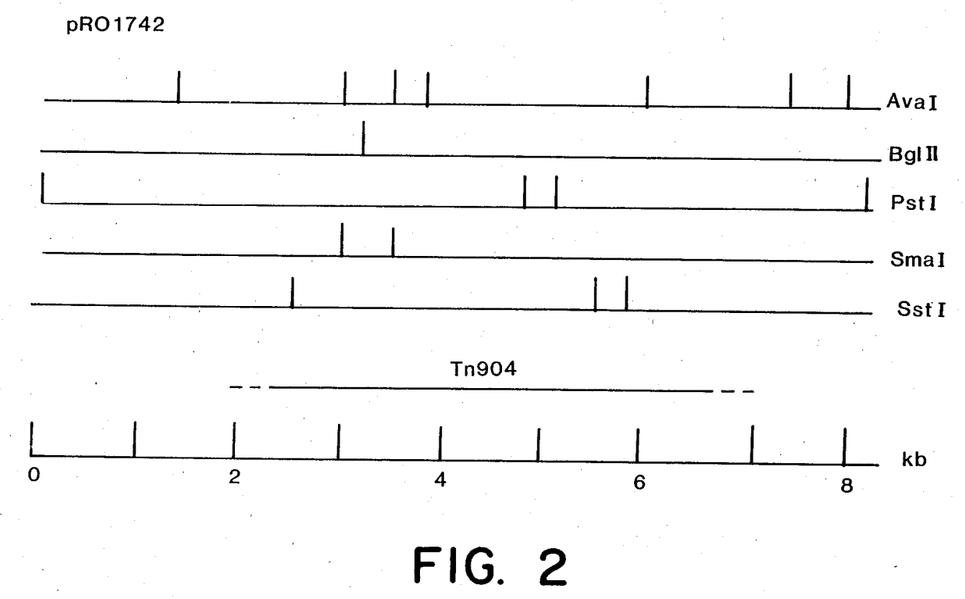
FIG. 2 shows a restriction endonuclease map of plasmid pRO1742.

Restriction sites on Tn904. DNA preparations of plasmid pRO1742 were cleaved with a variety of restriction endonucleases to partially characterize the DNA of Tn904. The results of these determinations done as described previously (Olsen, R. H., et al. J. Bacteriol. 150:60–69 (1982)) are shown in FIG. 2. No cleavage sites were observed for the restriction endonucleases EcoRI, HindIII, SalI, PvuII or BamHI. Further functional and physical mapping of Tn904 is discussed hereinafter.

The estimate of the size of Tn904 (5.2 kilobases) is derived from restriction endonuclease digests of the small plasmid, pRO1742 and other similarly Tn904-transposed plasmid isolates of pRO1600. In some instances, deletions in pRO1600 were observed concurrent with Tn904 transposition. However, the 5.2 Kb size-increase associated with Tn904 acquisition by pRO1600 was also observed when pBR322 Tn904 plasmids were examined. Deletions were also observed for Tn904-transposed larger plasmids, for example, plasmids RP1, FP2 or R388 after their acquisition of Tn904.

It is also possible that Ooms et al J. Bacteriol. 144:32–91 (1980)) were not measuring Tn904. A composite element similar to Tn4 might be present on pMG1. (Macrina, F. L., et al. Plasmid 1:417–420 (1978). Thus, these authors using the Ti plasmid may have observed this possibility. Alternatively, perhaps both Tn1 and Tn904 may have transposed from their donor plasmid which was a derivative of RP1. Translocation of intervening DNA as well as the two transposons could account for the variable size increase observed by these workers.

Tn904 is useful for studies on disparate Gram negative bacterial strains whose high intrinsic resistance to antibiotic resistance determinants found on other transposons precludes their utility. Its relatively small size, approximately equivalent to Tn1, may also facilitate these studies. Furthermore, its transposition frequency both in *E. coli* and *P. aeruginosa* resembles that of Tn1. Further experiments on the structure and function of Tn904 are discussed hereinafter.

EXAMPLE 3

Structure and Function of Tn904

Expression of streptomycin resistance. In the preceding Examples and discussion, the occurrence of a relatively large proportion of transposed derivatives of pBR322 when DNA was analyzed from strains containing both pBR322 and the transposon donor-plasmid, pRO169. At first glance, this was thought to reflect a high frequency of Tn904 transposition from pRO169 to pBR322 in the *Escherichia coli* bacterial strain used for these experiments. However, this result was not seen when *Pseudomonas aeruginosa* strains were studied using pRO1600, a small multi-copy plasmid (Olsen, R. H., et al, J. Bacteriol. 150:60–69(1982)). It was considered that since pBR322 is a multicopy plasmid, growth on medium which contained streptomycin may select for multicopy plasmids in *E. coli* which have acquired Tn904 to allow for greater expression of streptomycin resistance ($Sm^r$) which occurs as a function of gene dosage or copy number per cell. To evaluate this possible relationship, MIC (Minimal inhibitory concentration of antibiotic) determinations on bacterial strains with and without plasmids with Tn904 were done and the results are shown in Table 8.

TABLE 8

| MIC determinations for plasmids with Tn904. | | |
|---|---|---|
| | MIC value per trial[a] | |
| Bacterial Strain | I | II |
| *E. coli* | | |
| AE85 | <8 | <8 |
| AE85(pBR322) | <8 | <8 |
| AE85(pRO169) | 32 | 64 |
| AE85(pRO169/pBR322)-1 | 32 | 32 |
| AE85(pRO169/pBR322)-2 | 250 | 500 |
| AE85(pRO1744) | >1000 | >1000 |
| *P. aeruginosa* | | |

TABLE 8-continued

MIC determinations for plasmids with Tn904.

| Bacterial Strain | MIC value per trial[a] | |
|---|---|---|
| | I | II |
| PA02 | 32 | 32 |
| PA02(pMG1) | >1000 | >1000 |
| PA02(pRO169) | >1000 | >1000 |
| PA02(pRO1742) | >1000 | >1000 |

[a]MIC values were determined as described in Materials and Methods.

The results in Table 8 show no influence of plasmid pBR322 on the intrinsic resistance of AE85 to streptomycin and less expression of Sm$^r$ for AE85 (pRO169) than for PA02(pRO169). Plasmid pRO169 (RP1::Tn904) is a low copy number plasmid with approximately 2 copies per chromosome. Plasmid pRO1744 (pBR322::Tn904) on the other hand, confers a significantly higher level of streptomycin resistance to AE85 than does pRO169. We think this reflects its high copy number per cell and hence greater expression of the Sm$^r$ determinant. In *P. aeruginosa*, however, no such relationship obtained. The level of Sm$^r$ expression for limited copy number plasmids pMG1 or pRO169 was indistinguishable from the multicopy plasmid pRO1742 (pRO1600::Tn904). Therefore, in the preceding work, it appears that selection and passage of *E. coli* on a medium which contained streptomycin (25 μg/ml) favored the growth of those bacteria with pBR322::Tn904. Strain AE85(pRO169/pBR322)-1, shown in Table 8, which had not been serially transferred on medium with streptomycin shows a MIC value resembling that for AE85(pRO169). On the other hand, strain AE85(pRO169/pBR322)-2 shown in Table 8, which was serially transferred several times on medium with streptomycin, shows a high "apparent" MIC value reflecting selection for bacteria with pBR322::Tn904.

Figure 3:
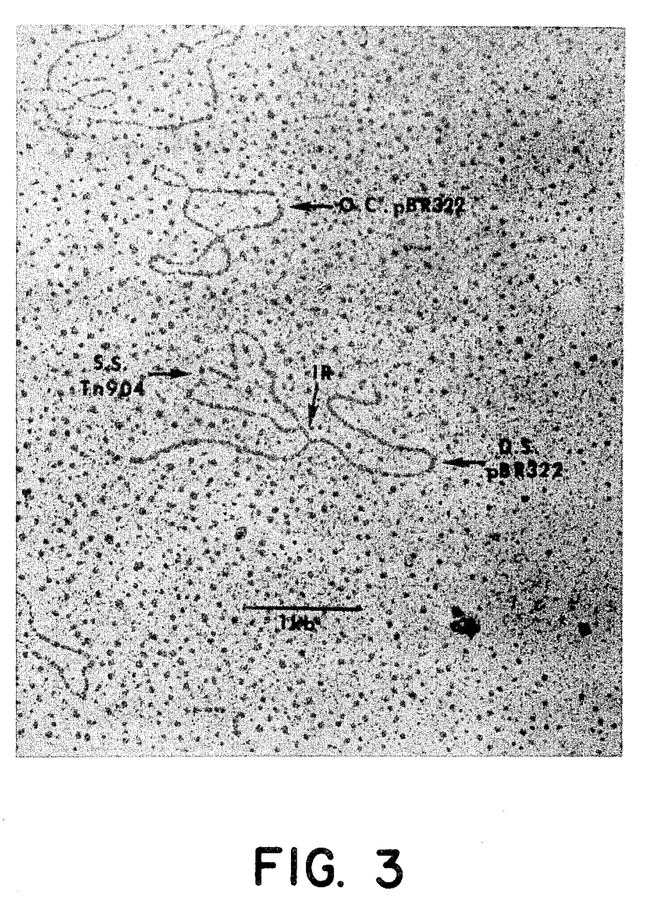
FIG. 3 shows an electron micrograph of a heteroduplex molecule formed between pBR322 and pRO1746. Samples were prepared and processed as described in Materials and Methods. Designations in FIG. 3 are as follows: S.S. Tn904, single-strand loop corresponding to Tn904; D.S. pBR322, double-stranded segments corresponding to pBR322; O.C. pBR322, open circular pBR322; IR, double-stranded, inverted repeated sequences at the point of insertion of Tn904 into pBR322; Kb, kilobase pairs.

Palindrome sequences of Tn904. In order to determine the size and nature of the palindromic sequences at the termini of Tn904, heteroduplex analysis was perforxed as described in the Materials and Methods section. For this, plasmid pRO1746 (pBR322::Tn904) was cleaved with the restriction endonuclease, GamHI, and heteroduplexed with pBR322 which had been cleaved with the same enzyme. Plasmid pBR322 DNA which had not been cleaved was added to the heteroduplex preparation to serve as an internal size standard. A typical heteroduplex figure, as observed with electron microscopy, is shown in FIG. 3. A number of molecules displaying stem-loop structures, as well as open circular pBR322 molecules were photographed and measured. The results of these measurements are shown in Table 9.

TABLE 9

Measurements of heteroduplex molecules formed between pRO1746 and pBR322[a]

| Molecule Description | Number Measured | Mean (Units) | Standard Deviation (Units) | Mean (bp) | Standard Deviation (bp) |
|---|---|---|---|---|---|
| pBR322 | 20 | 11.40 | 0.63 | 4362 | 241 |
| pBR322/pRO1746 heteroduplex stem | 22 | 0.32 | 0.08 | 124 | 27 |
| pBR322/pRO1746 shortest arm | 16 | 4.01 | 0.28 | 1530 | 110 |

[a]Preparation of samples and measurements were done as described in Materials and Methods.

Figure 4:
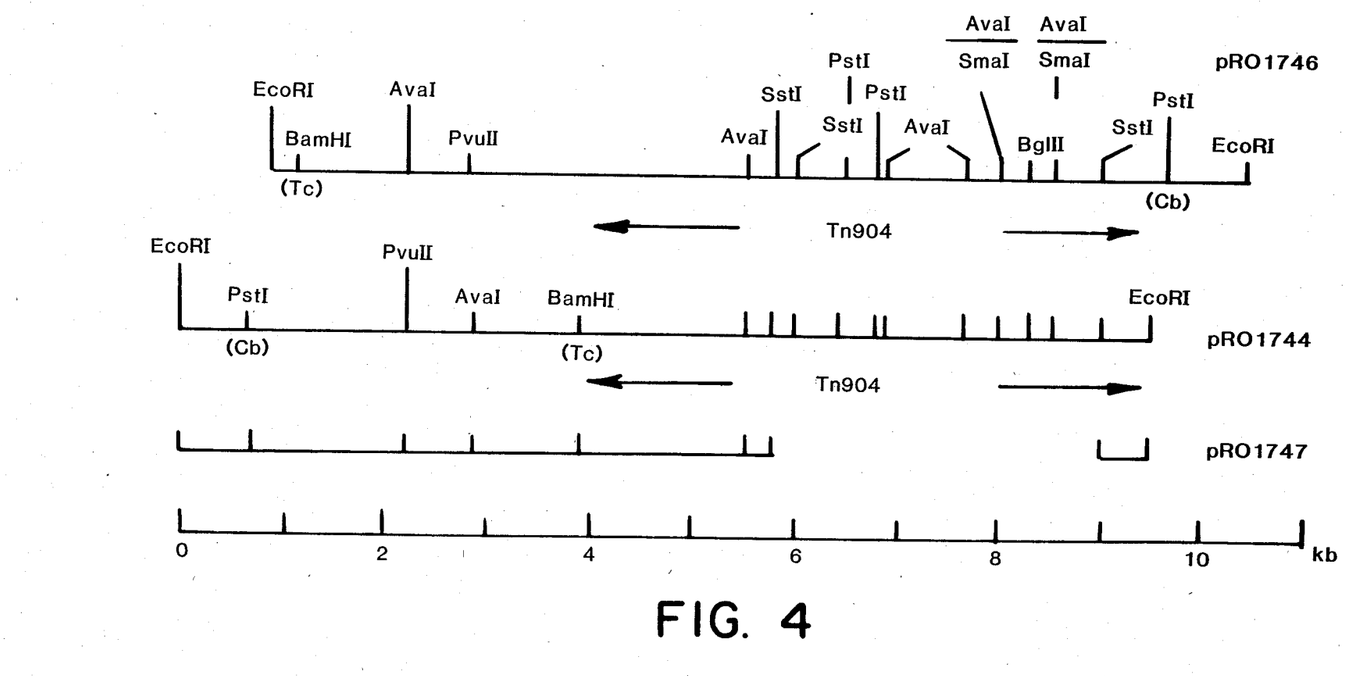
FIG. 4 shows restriction endonuclease maps of cloning vectors pRO1744, pRO1746 and pRO1747.

The data in Table 9 show that the stem structure of the heteroduplex consists of a region of approximately 126 base pairs (bp) and the morphology of the loop structure in relation to the stem as shown in FIG. 3 and other heteroduplemes seen resembles that expected for palindromic sequences that are in reverse orientation. Thus the palindromes of Tn904 and their orientation is similar to that observed for other transposons with short palindromic sequences, e.g., Tn3 (Heffron, F., et al, Cell 18:1153–1163(1979). These determinations also allowed an estimate of the location of the Tn904 insertion on the pBR322 molecule since the distance from the stem structure to the end of the molecule cleaved with BamHI could also be measured. Later, when pRO1746 was cleaved with other restriction endonucleases, the palindromes were then subsequently mapped in relation to cleavage sites within Tn904 and the BamHI site on pBR322. These distal ends of Tn904, mapped in relation to cleavage sites internal to the transposon, are shown in FIG. 4 as horizontal arrows.

Location of the Tn904 Sm$^r$ Determinant. Plasmid pRO1746 displayed at the top of FIG. 4 does not encode carbenicillin resistance (Cb$^r$) therefore reflecting the transposition of Tn904 into pBR322 at a site within the pBR322 determinant for beta-lactamase production. Analogously, pRO1744 shown in FIG. 4 displays a Tn904 transposition into pBR322 in reverse orientation to pRO1746 and this plasmid has lost tetracycline resistance (Tc$^r$) as a consequence of the insertion within the Tc region of pBR322. Plasmids such as these have been cleaved with restriction endonucleases with the derivation of the cleavage sites shown in FIG. 4 in relation to known sites for pBR322 and in relation to sites for plasmid pRO1600 shown previously (Olsen, R. H., et al. J. Bacteriol. 150:60–69 (1982)).

The region of Tn904 associated with the Sm$^r$ determinant was mapped. Plasmid pRO1744 was cleaved with the restriction endonuclease, SstI, following by agarose gel electrophoresis and electro-elution of the appropriate fragment which was then ligated and transformed into ED8654. Transformants typified by pRO1747 shown in FIG. 4, were found to have deleted most of the internal region of Tn904 and yet still encoded Sm$^r$. From this result it was surmised that the Sm$^r$ determinant was encoded within the left arm of Tn904 as shown in FIG. 4. The right arm seemed unlikely since the distance here between the SstI cleavage site and the distal end of the palindrome was approximately 250 bp and therefore limited to the production of a protein of less than 10,000 daltons.

Figure 5:
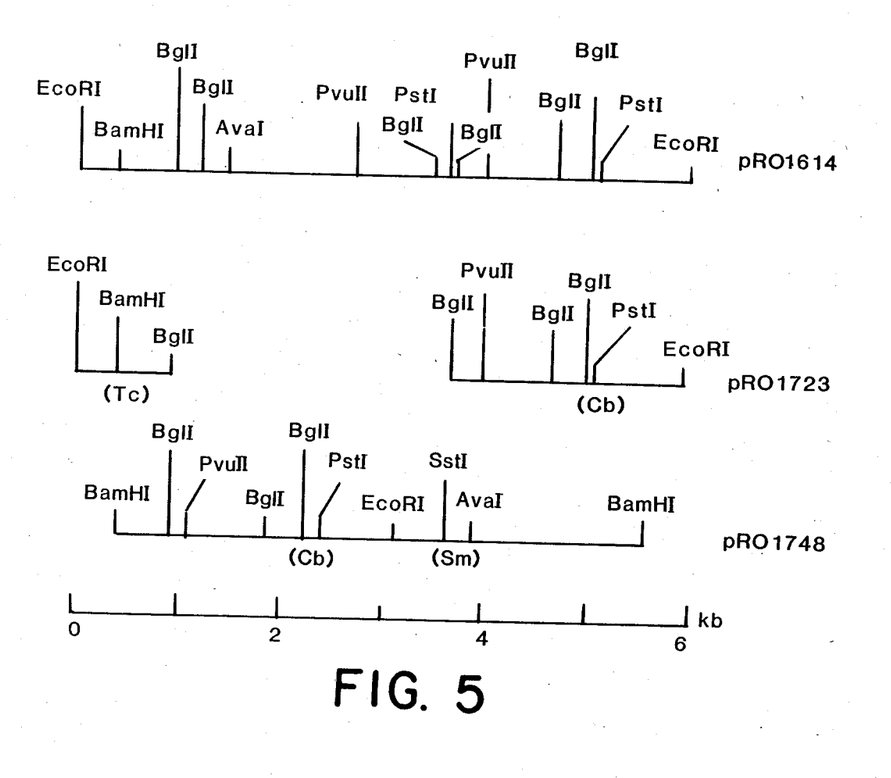
FIG. 5 includes restriction endonuclease maps showing the derivation of the cloning vector, pRO1723 and recombinant cloning vector, pRO1748 with the Sm$^r$ determinant of Tn904.

In view of the foregoing, the next objective was to determine if the AvaI cleavage site located in the left arm of the deleted Tn904 was included within the structural gene for Sm$^r$. For this a plasmid was needed with only the AvaI cleavage site located within the deleted Tn904 region of pRO1747. The location of the Sm determinant in Pseudomonas was evaluated since less equivocal scoring of $Sm^r$ independent of copy number of the vector was likely (See Table 8). Accordingly, we derived a plasmid, pRO1723, from Pseudomonas cloning vector, pRO1614 (Olsen, R. H., et al J. Bacteriol. 150:60–69 (1982)) U.S. patent application Ser. No. 147,563, filed May 8, 1980 as shown in FIG. 5. For this the pBR322 replicator region and part of the $Tc^r$ determinant of pBR322 was removed from pRO1614 by digestion with BglII, random reassociation of the cleavage fragments, ligation and then transformation into PA02. One such plasmid, designated pRO1723, is shown in FIG. 5 in relation to its progenitor, Plasmid pRO1614. Plasmid pRO1600 only contains the pRO1600 replicator, functional in Pseudomonas, and the pRO1614 determinant for $Cb^r$. The single AvaI cleavage site located within its progenitor, pRO1614, has been deleted.

To clone the region of pRO1747 which contained the $Sm^r$ determinant into pRO1723, both pRO1747 and pRO1723 were cleaved with BamHI and PstI, fragxents were allowed to reassociate and then ligated and transformed into PA02 with selection on TN medium which contained streptomycin (100 micrograms/ml). This strategy precluded the recovery of the parental $Sm^r$ plasmid, pRO1747, since its replicator (pBR322) is non-functional in Pseudomonas (Olsen, R. H., et al. J. Bacteriol. 150:60–69 (1982)). One transformant from this experiment, designated pRO1748 was analyzed as before and is shown at the bottom of FIG. 5. Its configuration was as anticipated for the replacement of the BamHI to PstI region of pRO1723 with the BamHI to PstI region from pRO1747 which contains the deleted Tn904 encloding $Sm^r$.

Figure 6:
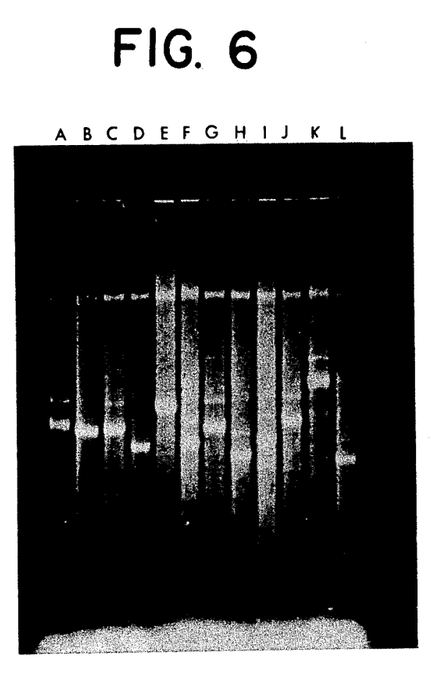
FIG. 6 is an agarose gel electrophoresis of recombinant cloning vectors with chromosomal DNA of PAO1c cloned into the AvaI site of pRO1748. File L shows the vector, pRO1748. Other files show plasmids which were streptomycin sensitive (Sm$^s$) when tested after their isolation.
Figure 7:
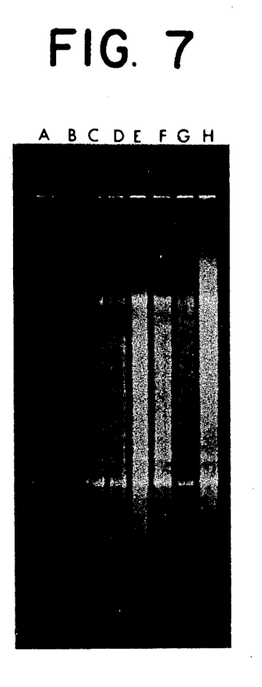
FIG. 7 is an agarose gel electrophoresis of cloning vectors which were Sm$^r$ after removal of their cloned PAO2 chromosome fragments. Files A and H show the vector, pRO1748. The other files show DNA from transformants derived from either of two recombinant plasmids shown in FIG. 4.

Plasmid pRO1748, derived as described above, was now used to clone *P. aeruginosa* chromosomal DNA cleaved with AvaI as reported previously for other restriction endonucleases (Olsen, R. H., et al. J. Bacteriol. 150:60–69 (1982)). AvaI cleaved DNA was mixed with pRO1748 treated similarly, ligated and transformed into strain PA02 with selection for $Cb^r$. Three hundred (300) such transformants were then tested for $Sm^r$ and 25 isolates were streptomycin sensitive ($Sm^s$) and thus presumably had chromosomal DNA incorporated into their AvaI cleavage site. Several of the $Sm^s$ transformants were lysed and their DNA extracted and electrophoresed as described in Materials and Methods. These results are shown in FIG. 6. File L shows the vector, pRO1748, and the other files display $Sm^s$ plasmids clearly larger than the vector. To test for the reconstitution of the $Sm^r$ determinant after the removal of DNA cloned into the AvaI site, two of these $Sm^s$ transformants were used to prepare purified DNA for cleavage with AvaI, reassociation, ligation and their subsequent transformation into PA02. Fifty transformants derived from each DNA preparation were selected for $Cb^r$ and subsequently tested for their reconstitution of $Sm^r$. DNA from the $Sm^r$ transformants is shown in FIG. 7. Files A and H are the vector, pRO1748, files B, C, D or E, F, G are from transformants derived from the two DNA preparations respectively. From one such DNA preparation, most transformants selected for $Cb^r$ were now also $Sm^r$; from the other DNA preparation, 4 of the transformants had reconstituted $Sm^r$. Thus, removal of the cloned chromosomal DNA from the AvaI cleavage site of the Tn904-derived fragment re-established $Sm^r$ and therefore the AvaI cleavage site is located within the region of Tn904 encoding $Sm^r$.

Two aminoglycoside modifying enzymes have been shown to be associated with $Sm^r$ enclosed by plasmids (Benveniste, R., et al. Annu. Revs. Biochem. 42:471–506 (1973)), streptomycin-spectinomycin adenylyltransferase or streptomycin phosphotransferase and the latter has been shown for Pseudomonas bacteria (Kobayashi, F., et al. Japan. J. Microbiol. 16:15–19 (1972). Examples of both types of activities have been associated with transposons. Barth et al. J. Bacteriol. 125:800–810 (1976)) have described Tn7 which encodes $Sm^r$, spectinomycin resistance ($Sp^r$) and trimethoprim resistance ($Tp^r$) with $Sm^r$ and $Sp^r$ associated with adenylyltransferase activity (Benveniste, R., et al. Annu. Revs. Biochem. 42:471–506 (1973)). Kopecko and Cohen. Proc. Nat. Acad. Sci. USA 72:1373–1377 (1975)) described Tn4 which also encodes $Sm^r$ and $Sp^r$. Hedges et al. Gene 1:241–253 (1977)) have described the properties of a transposon conferring resistance to penicillins and streptomycin which they designated TA beta. This transposon, encoding phosphotransferase (Hedges, R., et al. Gene 1:241–253 (1977), was derived from R938, a broad host range P incompatibility group plasmid (Hedges, R., et al. J. Gen. Microbiol. 86:88–92 (1975). More recently, however, Rubens et al. J. Bacteriol. 139:877–882 (1979)) have described Tn1696 which encodes multiple resistances to aminoglycoside antibiotics but not $Sp^r$ and therefore its $Sm^r$ also derives from phosphotransferase activity. This transposon was originally isolated in Pseudomonas. The Tn904, also lacks $Sp^r$ and therefore likely encodes phosphotransferase activity as observed for Tn1696 based on the relationship described by Benveniste R., et al. Annu. Revs. Biochem. 42:471–506 (1973)). However, Tn904 differs from Tn1696 in that it only encodes $Sm^r$ and not resistance to other antibiotics or mercuric ions. Therefore, Tn904 is unique in its phenotype although it resembles another Pseudomonas transposon lacking $Sp^r$.

Nordstrom, K., et al. J. Bacteriol. 110:562–569 (1972) and later Uhlin, D., et al. Plasmid 1:1–7 (1977) showed that there is a linear correlation between enzyme synthesis and number of gene copies and also a linear correlation between resistance and enzyme production (Nordstrom, K., et al. J. Bacterio 110:562–569 (1972). This was demonstrated for copy number mutants of the R-plasmid, R1drd-19, where frequency of conjugal transfer, resistance to antibiotics and the production of the corresponding enzymes were shown to correlate with copy number. In this regard, the antibiotic resistances and the production of cognate enzymes active on ampicillin, chloramphenicol and streptomycin were examined. In the present work a similar correlation was observed for strains when MIC values for pRO169 (RP1:Tn904) and pRO1746 (pBR322::Tn904) were compared. Nordstrom K., et al. J. Bacteriol. 110:562–569 (1972) suggest that inefficient penetration of the antibiotic, streptomycin, may partially account for such a difference in MIC values because minute changes in enzyme activity within the cell wall will cause a considerable increase in the level of resistance. In any case, however the relationship between copy number and the level of $Sm^r$ was not observed in Pseudomonas bacteria and this may be yet another reflection of the disparate properties of Pseudomonas in relation to *E. coli*.

Heteroduplex analysis of pRO1746 with pBR322 showed that Tn904 is flanked by inverted repeat sequences of about 126 base pairs. However, as suggested by Heffron, F., et al. Proc. Nat. Acad. Sci. USA 72:3623–3627 (1975)), this should be taken only as a maximum value since various estimates of the size of the tnA inverted repeats gave results of 140 base pairs (Heffron, F., et al. Proc. Nat. Acad. Sci. USA 72:3623–3627 (1975) Kopecko, D. J., et al. Proc. Nat. Acad. Sci. USA 72:1373–1377 (1975)) while DNA sequence analysis showed that the repeats were only 38 base pairs in length (Heffron, F., et al. Cell 18:1153–1163 (1979); Rubens, C., et al. J. Bacteriol. 139:877–882 (1979). However, present studies do show that Tn904 resembles the group of transposable elements which have short distal repeated DNA sequences.

A region of Tn904 has been shown to be associated with its Sm$^r$ determinant. This was facilitated by the development of a cloning vector, pRO1723, for this purpose from the Pseudomonascloning vector, pRO1614. When recombinant plasmids were constructed in vitro which contained a region of Tn904 encoding Sm$^r$, it was shown that insertion of hetero-DNA into an AvaI restriction endonuclease cleavage site within the Tn904-derived region of the recombinant plasmids resulted in the loss of Sm$^r$. Furthermore, the removal of the inserted DNA resulted in the reconstitution of the Sm$^r$ determinant. Thus, the Sm$^r$ determinant from Tn904 has utility for the development cloning vectors useful for the isolation and characterization of DNA cleaved with AvaI. This may be particularly useful for Pseudomonas bacteria which show high intrinsic resistances to the antibiotics ampicillin/carbenicillin, chloramphenicol or kanamycin precluding the inclusion of these markers in vectors for self-cloning in Pseudomonas and related bacteria has been shown previously for *P. aeruginosa* (Olsen, R. H., et al. J. Bacteriol. 150:60–69 (1982)).

As can be seen from the preceding description, novel Tn904 containing cloning vectors were prepared. Essentially they contain that portion of the Tn904 encoding for Sm$^r$ resistance.

I claim:

1. In a method including transposing a transposon by mating bacterial cells wherein the first cell contains the transposon in a first plasmid and the second cell contains a second plasmid which is receptive to the transposon the improvement which comprises:
   (a) transposing transposon Tn904 in a first plasmid PLASMID-1::Tn904 to a second vector plasmid receptive to the transposon to form a second transconjugant plasmid VECTOR PLASMID-2::Tn904, wherein Tn904 encodes for streptomycin resistance in a site cleaved by AvaI, wherein the second vector plasmid is selected from a Pseudomonas or Escherichia vector plasmids and wherein the VECTOR PLASMID-2::Tn904 is transformable; and
   (b) cleaving the Tn904 with AvaI and ligating a segment of DNA into the cleaved site to produce a recombinant plasmid.

2. The method of claim 1 wherein PLASMID-1::Tn904 is pRO161:Tn904 as carried in *Pseudomonas aeruginosa* NRRL-B-15313 (pRO165).

3. The method of claim 1 wherein PLASMID-1::Tn904 is RP-1::Tn904 as carried in *Pseudomonas aeruginosa* NRRL-B-15319 (pRO169).

4. The method of claim 1 wherein PLASMID-1::Tn904 is RP1::Tn904 as carried in *Pseudomonas aeruginosa* NRRL-B-15319 (pRO169), wherein the second vector plasmid is pRO1600 as carried in *Pseudomonas aeruginosa* NRRL-B-15314 and wherein VECTOR PLASMID-2::Tn904 is pRO1600::Tn904 as carried in *Pseudomonas aeruginosa* NRRL-B-15176 (pRO1642) or NRRL-B-15317 (pRO1643).

5. The method of claim 1 wherein PLASMID-1::Tn904 is RP1::Tn904 as carried in *Pseudomonas aeruginosa* NRRL-B-15319 (pRO169), wherein the second plasmid is pBR322 as carried in *E. coli* NRRL-B-15320 and wherein VECTOR PLASMID-2::Tn904 is pBR322::Tn904 as carried in *E. coli* NRRL-B-15321 (pRO1744), NRRL-B-15322 (pRO1745) or NRRL-B-15323 (pRO1746).

6. The method of claim 1 wherein a portion of the VECTOR PLASMID-2::Tn904 is removed with an endonuclease and religated to form a second VECTOR PLASMID which retains the AvaI site.

7. The method of claim 6 wherein in addition a portion of the plasmid carried in *E. coli* NRRL-B-15321 (pRO1744) is removed with endonuclease SstI, ligated and retransferred to produce a vector plasmid pRO17-47as carried in *E. coli* NRRL-B-15324.

8. The method of claim 6 wherein in addition pRO1614 as carried in *Pseudomonas aeruginosa* NRRL-B-15315 is digested with endonuclease BglI and religated to form plasmid pRO1723 as carried in *Pseudomonas aeruginosa* NRRL-B-15316 and then pRO1723 and pRO1747 are cleaved together with BamHI and PstI to produce pRO1748 is carried in *Pseudomonas aeruginosa* NRRL-B-15318 which retains Tn904 and which has a single endonuclease AvaI cleavage site in Tn904.

9. The method of claim 1 wherein the first and second cells are of the genus Pseudomonas.

10. The method of claim 1 wherein the first and second cells are *Pseudomonas aeruginosa*.

11. The method of claim 10 wherein the first plasmid is pRO161:Tn904 as carried in *Pseudomonas aeruginosa* NRRL-B-15313 (pRO165).

12. The method of claim 1 wherein the first and second cells are of the same genus and wherein the cells are substantially free of contaminating non-transposing cells.

13. The method of claim 1 wherein the vector is between about 5 and 10 kilobase pairs in length.

14. The method of claim 1 wherein VECTOR PLASMID-2:Tn904 is pRO 1723 carried in *Pseudomonas aeruginosa* NRRL-B-15316.

15. The method of claim 1 wherein VECTOR PLASMID-2:Tn904 is pRO 1748 as carried in *Pseudomonas aeruginosa* NRRL-B-15318.

16. The method of claim 1 wherein VECTOR PLASMID-2:Tn904 contains at least one second AvaI cleavage site and including the additional step of removing the second AvaI cleavage site without removing the Tn904 AvaI cleavage site.

17. A transformable cloning vector plasmid derived from VECTOR PLASMID::Tn904 including deoxyribonucleic acid which encodes for streptomycin resistance in a site cleaved by AvaI and derived from Tn904 combined with a vector plasmid selected from Pseudomonas or Escherichia vector plasmids, wherein the site has been cleaved with AvaI and a segment of DNA introduced and ligated to produce a recombinant plasmid.

18. The vector plasmid of claim 17 wherein the deoxyribnucleic acid has a length between about 5 to 10 kilobase pairs.

19. The vector plasmid of claim 17 wherein the vector plasmid is derived from pRO1600 as carried in Pseudomonas aerginosa NRRL-B-15314.

20. The vector plasmid of claim 17 wherein the vector plasmid deoxyribonucleic acid is derived from pBR-322 as carried in *E. coli* NRRL-B-15320.

21. The vector plasmid of claim 17 wherein the vector plasmid is derived through transposition of Tn904 to a parent vector plasmid.

22. The vector plasmid of claim 17 which is pRO 1723 as carried in *Pseudomonas aeruginosa* NRRL-B-15316.

23. The vector plasmid of claim 17 which is pRO 1748 as carried in *Pseudomonas aeruginosa* NRRL-B-15318.

24. A method for cloning DNA which comprises:
   (a) providing a transformable VECTOR PLASMID:Tn904 having streptomycin resistance in a site cleaved by AvaI and derived from Tn904 combined with a vector plasmid selected from Pseudomonas or an Escherichia vector plasmids; and
   (b) cleaving the Tn904 with AvaI and ligating a segment of DNA into the cleaved site to produce a recombinant plasmid.

25. The method of claim 24 wherein the vector plasmid is selected from pBR322 and pRO1600.

* * * * *

UNITED STATES PATENT AND TRADEMARK OFFICE
CERTIFICATE OF CORRECTION

PATENT NO. : 4,567,141          Page 1 of 2
DATED       : 1986 January 28
INVENTOR(S) : Ronald H. Olsen It is certified that error appears in the above-identified patent and that said Letters Patent are hereby corrected as shown below:

Column 2, line 39, "Van Gijsegem" should be --Van Gijisegem--.
Column 2, line 61, "tumefacinens" should be --tumefaciens--.
Column 6, line 15, "nd" should be --and--.
Column 7, line 10, "(177)" should be --(1977)--.
Column 9, line 50, "PAO203(pMG1)" should be --PAO2003(pMG1)--.
Column 9, line 53, "PAO38" should be --PAO33--.
Column 11, line 12 "SM$^4$" should be --SM$^r$--.
Column 13, lines 42 and 43 "perforxed" should be --performed--.
Column 14, line 17 "heteroduplemes" should be --heteroduplexes--.
Column 15, line 13 "progenitor, Plasmid PRO1614" should be --progenitor pRO 1614--.
Column 15, line 22 "fragxents" should be --fragments--.
Column 15, line 35, "encloding" should be --encoding--.
Column 17, line 18 "Pseudomonascloning" should be --Pseudomonas cloning--.

UNITED STATES PATENT AND TRADEMARK OFFICE
CERTIFICATE OF CORRECTION

PATENT NO. : 4,567,141

DATED : 1986 January 28

INVENTOR(S) : Ronald H. Olsen

Page 2 of 2

It is certified that error appears in the above-identified patent and that said Letters Patent is hereby corrected as shown below:

Column 18, line 29 "is" should be --as--.
Column 19, line 4 "aerginosa" should be --aeruginosa--.

Signed and Sealed this

Twenty-sixth Day of August 1986

[SEAL]

Attest:

DONALD J. QUIGG

Attesting Officer

Commissioner of Patents and Trademarks